US012788860B2

(12) United States Patent
Jones et al.

(10) Patent No.: US 12,788,860 B2
(45) Date of Patent: *Nov. 10, 2026

(54) FILTERING SYSTEMS AND FILTERING MANIFOLDS FOR USE WITH FILTERING SYSTEMS

(71) Applicant: PHARAOH NEURO, INC., Minneapolis, MN (US)

(72) Inventors: Justin Charles Jones, Minneapolis, MN (US); Matthew John Hill, St. Paul, MN (US); Elizabeth Christine Johnson, Minneapolis, MN (US); Brett Jacob Andreas, Minneapolis, MN (US); Lucas John Sheehan, Shakopee, MN (US); Nathan Mueggenberg, Coon Rapids, MN (US); Chase Knight-Scott, Tyrone, GA (US); David John Deroode, Crystal, MN (US)

(73) Assignee: PHARAOH NEURO, INC.

( * ) Notice: Subject to any disclaimer, the term of this patent is extended or adjusted under 35 U.S.C. 154(b) by 0 days.

This patent is subject to a terminal disclaimer.

(21) Appl. No.: 18/658,381

(22) Filed: May 8, 2024

(65) Prior Publication Data

US 2024/0285840 A1 Aug. 29, 2024

Related U.S. Application Data

(63) Continuation of application No. 17/332,180, filed on May 27, 2021, now Pat. No. 12,005,171.

(Continued)

(51) Int. Cl.

*A61M 1/34* (2006.01)
*A61M 1/36* (2006.01)

(52) U.S. Cl.

CPC ............ *A61M 1/3496* (2013.01); *A61M 1/34* (2013.01); *A61M 1/36* (2013.01);

(Continued)

(58) Field of Classification Search

CPC .......... A61M 27/006; A61M 2027/004; A61M 2205/75; A61M 2202/0464;

(Continued)

(56) References Cited

U.S. PATENT DOCUMENTS 4,161,264 A * 7/1979 Malmgren ............... G05D 7/03 222/440
4,666,598 A 5/1987 Heath et al.

(Continued)

FOREIGN PATENT DOCUMENTS

CN 2427267 Y 4/2001
CN 101601970 A 12/2009

(Continued)

OTHER PUBLICATIONS

International Search Report and Written Opinion dated Jun. 28, 2021 for International Application No. PCT/US2021/016401.

(Continued)

*Primary Examiner* — Philip R Wiest
*Assistant Examiner* — Seth Han
(74) *Attorney, Agent, or Firm* — Seager, Tufte & Wickhem LLP

(57) ABSTRACT

Filtering device for filtering cerebrospinal fluid are disclosed. An example filtering device may include a filter housing having an inlet for receiving cerebrospinal fluid from a patient and an outlet for returning filtered cerebrospinal fluid to the patient. The filter housing may include a plurality of layers coupled together and defining a fluid pathway therein between the inlet and the outlet. A filtering section may be defined within the filter housing along the (Continued)

fluid pathway. The filtering section may include a widened region of the fluid pathway that is configured to slow the passage of fluid therethrough.

20 Claims, 15 Drawing Sheets

Related U.S. Application Data

(60) Provisional application No. 63/031,319, filed on May 28, 2020.

(52) U.S. Cl.
CPC ................. *A61M 1/362263* (2022.05); *A61M 2202/0464* (2013.01); *A61M 2205/3331* (2013.01); *A61M 2205/75* (2013.01)

(58) Field of Classification Search
CPC .. A61M 2205/3334; A61M 2205/3331; A61M 2205/3358; A61M 1/1561; A61M 1/156; A61M 1/1562; A61M 1/154; A61M 1/15; A61M 2205/12; A61M 2205/125; A61M 2205/126; A61M 1/15625; F04B 43/02
See application file for complete search history.

(56) References Cited

U.S. PATENT DOCUMENTS 4,756,705 A 7/1988 Beijbom et al.
4,767,526 A * 8/1988 Vantard ............... A61M 1/1694 210/257.2
4,904,237 A 2/1990 Janese
5,460,490 A 10/1995 Carr et al.
5,609,572 A * 3/1997 Lang ................. A61M 5/14224 604/22
5,640,995 A 6/1997 Packard et al.
5,824,217 A 10/1998 Pearl et al.
6,013,051 A * 1/2000 Nelson .............. A61M 39/0208 604/93.01
6,561,997 B1 * 5/2003 Weitzel ................... A61M 1/34 604/4.01
6,638,478 B1 10/2003 Treu et al.
6,660,171 B2 12/2003 Zuk, Jr.
7,712,360 B2 * 5/2010 Jones .................... A61M 1/734 604/317
10,632,237 B2 4/2020 Meyering et al.
10,695,545 B2 6/2020 Hedstrom et al.
10,850,235 B2 12/2020 Meyering et al.
11,577,060 B2 2/2023 Hedstrom et al.
12,005,171 B2 * 6/2024 Jones ...................... A61M 1/88
2002/0008063 A1 1/2002 Zuk, Jr.
2002/0147423 A1 10/2002 Burbank et al.
2004/0024358 A1 2/2004 Meythaler et al.
2009/0084721 A1 4/2009 Yardimci et al.
2010/0116740 A1 5/2010 Fulkerson et al.
2011/0036787 A1 2/2011 Deutsch et al.
2011/0046558 A1 2/2011 Gravesen et al.
2012/0184940 A1 7/2012 Mng et al.
2012/0316492 A1 * 12/2012 Chappel ............... G05D 7/0694 604/67
2013/0129541 A1 5/2013 Flanary
2013/0267892 A1 * 10/2013 Woolford ........... A61B 17/1659 604/319
2014/0207045 A1 7/2014 Anand et al.
2014/0220617 A1 8/2014 Yung et al.
2016/0030658 A1 * 2/2016 van der Merwe ........................... A61M 1/362265 604/67
2017/0035950 A1 2/2017 Meyering et al.
2017/0072161 A1 3/2017 Iwatschenko et al.
2017/0157374 A1 * 6/2017 Hedstrom ........... A61M 27/006
2018/0001009 A1 1/2018 Crawford et al.
2018/0093270 A1 4/2018 Ladtkow et al.
2018/0235523 A1 * 8/2018 Sauder .................. A61M 5/142
2019/0030486 A1 1/2019 Leuthold et al.
2019/0105475 A1 4/2019 Lad et al.
2019/0298231 A1 10/2019 Grant et al.
2019/0316948 A1 10/2019 Karol et al.
2019/0366326 A1 12/2019 Volland
2020/0001059 A1 1/2020 Campbell et al.
2021/0052866 A1 * 2/2021 Roberts ............... A61M 27/006
2021/0236781 A1 8/2021 Darbandi et al.

FOREIGN PATENT DOCUMENTS

CN 105079891 A 11/2015
CN 207587789 U 7/2018
EP 117695 A2 9/1984
JP S62172965 A 7/1987
JP 2018537191 A 12/2018
WO 2015131087 A1 9/2015
WO 2017096228 A1 6/2017

OTHER PUBLICATIONS

Invite to Pay Additional Fees dated Sep. 16, 2021 for International Application No. PCT/2021/034487.

* cited by examiner

FILTERING SYSTEMS AND FILTERING MANIFOLDS FOR USE WITH FILTERING SYSTEMS

CROSS-REFERENCE TO RELATED APPLICATIONS

This application is a continuation of U.S. application Ser. No. 17/332,180, filed, May 27, 2021, which claims priority to U.S. Provisional Application Ser. No. 63/031,319, filed May 28, 2020, the entirety of which is incorporated herein by reference.

TECHNICAL FIELD

The present disclosure relates to filtering manifolds, filtering systems, and methods for treating along the central nervous system.

BACKGROUND

A wide variety of medical devices have been developed for medical use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. A filtering device for filtering cerebrospinal fluid is disclosed. The filtering device comprises: a filter housing having an inlet for receiving cerebrospinal fluid from a patient and an outlet for returning filtered cerebrospinal fluid to the patient; wherein the filter housing includes a plurality of layers coupled together and defining a fluid pathway therein between the inlet and the outlet; a filtering section defined within the filter housing along the fluid pathway; and wherein the filtering section includes a widened region of the fluid pathway that is configured to slow the passage of fluid therethrough.

Alternatively or additionally to any of the embodiments above, the filter housing includes three or more layers.

Alternatively or additionally to any of the embodiments above, the filter housing includes four or more layers.

Alternatively or additionally to any of the embodiments above, the filter housing includes five or more layers.

Alternatively or additionally to any of the embodiments above, the widened region of the fluid pathway defines a gravity filtration section.

Alternatively or additionally to any of the embodiments above, the filtering section includes a filter disk member.

Alternatively or additionally to any of the embodiments above, the filter disk member includes a dead-end filter disk.

Alternatively or additionally to any of the embodiments above, the filter disk member is disposed between two adjacent layers of the filter housing.

Alternatively or additionally to any of the embodiments above, further comprising one or more sensors coupled to the filter housing.

Alternatively or additionally to any of the embodiments above, further comprising a membrane disposed between two adjacent layers of the filter housing.

Alternatively or additionally to any of the embodiments above, the filter housing includes a curved region.

Alternatively or additionally to any of the embodiments above, the curved region is disposed along a top surface of the filter housing.

Alternatively or additionally to any of the embodiments above, further comprising a handle coupled to the filter housing.

Alternatively or additionally to any of the embodiments above, the handle includes one or more latching projections.

Alternatively or additionally to any of the embodiments above, the handle is configured to shift between a first position and a second position.

Alternatively or additionally to any of the embodiments above, when the handle is in the first position, the latching projections are in disengaged arrangement and wherein when the handle is in the second position, the latching projections are in an engaged arrangement.

Alternatively or additionally to any of the embodiments above, the filtering device is coupled to a controller assembly.

Alternatively or additionally to any of the embodiments above, when the handle is in the second position, the latching projections are engage a latching region of the controller assembly.

Alternatively or additionally to any of the embodiments above, a side section of the filter housing includes a pump region.

Alternatively or additionally to any of the embodiments above, the pump region includes a first connector, a second connector, and a tube extending between the first connector and the second connector.

Alternatively or additionally to any of the embodiments above, further comprising a sampling port coupled to the filter housing.

Alternatively or additionally to any of the embodiments above, the sampling port is in fluid communication with the inlet.

Alternatively or additionally to any of the embodiments above, the sampling port is in fluid communication with the inlet.

Alternatively or additionally to any of the embodiments above, the sampling port is in fluid communication with a waste pathway.

A filtering device for filtering cerebrospinal fluid is disclosed. The filtering device comprises: a filter housing having an inlet for receiving cerebrospinal fluid from a patient, an outlet for returning filtered cerebrospinal fluid to the patient, and a curved orienting surface for orienting the filter housing relative to a controller assembly; wherein the filter housing includes a plurality of layers including a first layer, a second layer, a third layer, and a fourth layer; one or more sensors disposed along the first layer; a membrane disposed between the first layer and the second layer; and a filter disk disposed between the third layer and the fourth layer.

A filtering device for filtering cerebrospinal fluid is disclosed. The filtering device comprises: a filter housing having an inlet for receiving cerebrospinal fluid from a patient and an outlet for returning filtered cerebrospinal fluid to the patient; wherein the filter housing includes a plurality of layers, the plurality of layers define a fluid pathway between the inlet and the outlet; a first filter disposed between two adjacent layers of the filter housing; and a second filter defined at least in part by an enlargement in the fluid pathway.

A filtering device for filtering cerebrospinal fluid is disclosed. The filtering device comprises: a filter housing formed from a plurality of discrete layers coupled together and defining a fluid pathway therein; and a filtering section defined by a widened region of the fluid pathway that is configured to slow the passage of fluid therethrough in order to allow gravity filtration of fluid passing therethrough.

Alternatively or additionally to any of the embodiments above, the filter housing includes three or more layers.

Alternatively or additionally to any of the embodiments above, the filter housing includes four or more layers.

Alternatively or additionally to any of the embodiments above, the filter housing includes five or more layers.

Alternatively or additionally to any of the embodiments above, further comprising a filter disk member disposed between two adjacent layers of the filter housing.

Alternatively or additionally to any of the embodiments above, the filter disk member includes a dead-end filter disk.

Alternatively or additionally to any of the embodiments above, further comprising one or more sensors coupled to the filter housing.

Alternatively or additionally to any of the embodiments above, further comprising a membrane disposed between two adjacent layers of the filter housing.

Alternatively or additionally to any of the embodiments above, the filter housing includes a curved region.

Alternatively or additionally to any of the embodiments above, the curved region is disposed along a top surface of the filter housing.

Alternatively or additionally to any of the embodiments above, further comprising a handle coupled to the filter housing.

Alternatively or additionally to any of the embodiments above, the handle includes one or more latching projections.

Alternatively or additionally to any of the embodiments above, the handle is configured to shift between a first position and a second position.

Alternatively or additionally to any of the embodiments above, when the handle is in the first position, the latching projections are in disengaged arrangement and wherein when the handle is in the second position, the latching projections are in an engaged arrangement.

Alternatively or additionally to any of the embodiments above, the filtering device is coupled to a controller assembly.

Alternatively or additionally to any of the embodiments above, when the handle is in the second position, the latching projections are engage a latching region of the controller assembly.

Alternatively or additionally to any of the embodiments above, a side section of the filter housing includes a pump region.

Alternatively or additionally to any of the embodiments above, the pump region includes a first connector, a second connector, and a tube extending between the first connector and the second connector.

Alternatively or additionally to any of the embodiments above, further comprising a sampling port coupled to the filter housing.

A filtering device for filtering cerebrospinal fluid is disclosed. The filtering device comprises: a filter housing having an inlet for receiving cerebrospinal fluid from a patient and an outlet for returning filtered cerebrospinal fluid to the patient; wherein the filter housing includes a plurality of layers coupled together and defining a fluid pathway therein between the inlet and the outlet; a filtering section defined within the filter housing along the fluid pathway; a membrane disposed between two adjacent layers of the filter housing, the membrane being configured to seal the fluid pathway within the filter housing while allowing pressure to be sensed; and wherein the filtering section includes a widened region of the fluid pathway that is configured to slow the passage of fluid therethrough.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
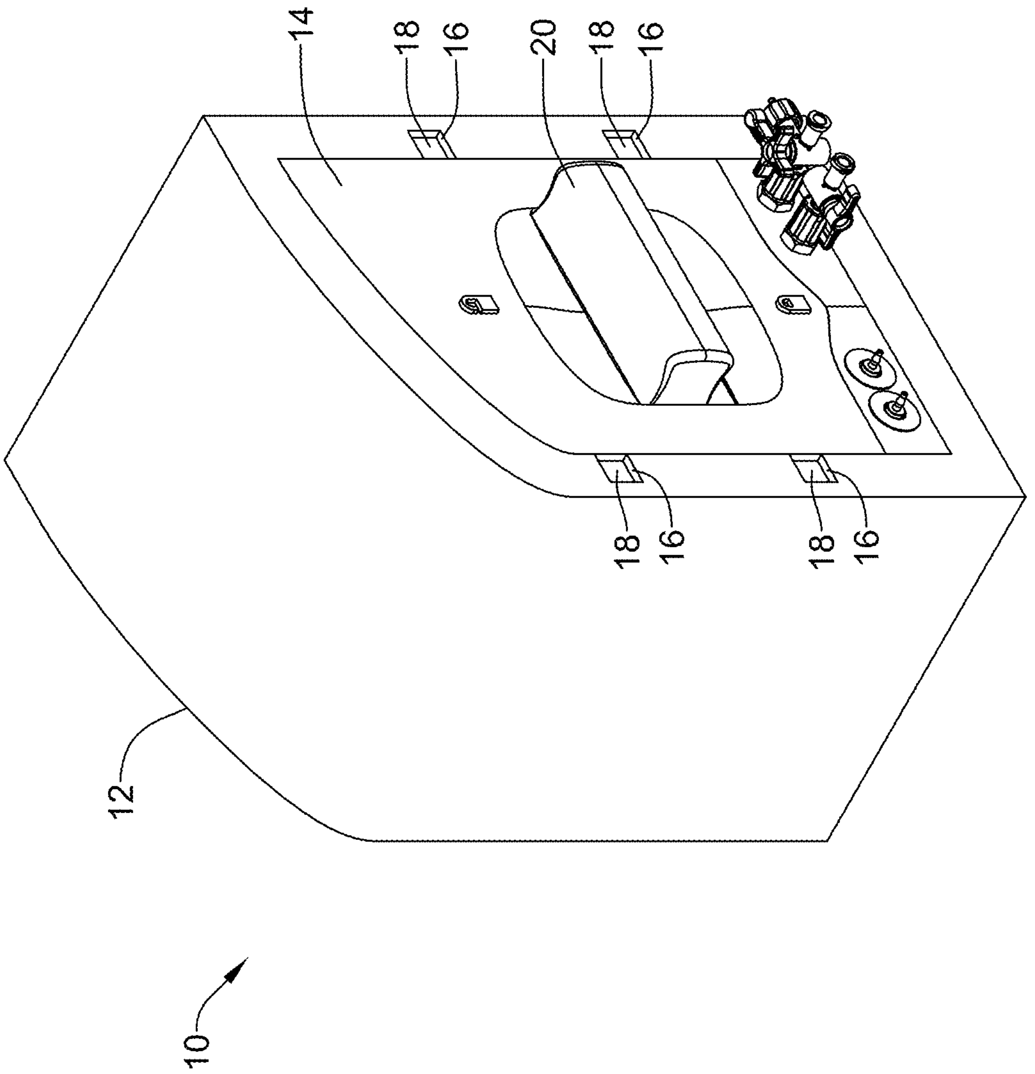
FIG. 1 is a perspective view of a portion of an example filtering system in a first configuration.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Cerebrospinal fluid (CSF) is a generally clear, colorless fluid with viscosity similar to water that is produced within the choroid plexus located in the ventricles of the brain. Total CSF volume has been estimated to range from approximately 150 to 300 milliliters in healthy adults. The choroid plexus is believed to produce approximately 500 milliliters of CSF daily in order to accommodate flushing or recycling of CSF to remove toxins and metabolites. The total volume of CSF is replenished several times per day or possibly more during sleep cycles and other activities. CSF also serves to float the delicate brain tissue by the Archimedes principle, and it protects the brain from sudden movements by cushioning the tissue. From the choroid plexus, CSF flows slowly through a series of openings into the space surrounding the brain and spinal column, and then into the body through multiple outflow pathways that include arachnoid granulations, cribiform plate, dural lymphatics, spinal cord nerve root sleeves, and possibly other pathways within the brain tissue. CSF is found in the space between the pia mater and the arachnoid mater, known as the subarachnoid space and also located within the ventricular system of the brain and in a series of cisterns located external to the brain. In addition to the net production and absorption of CSF flow, the CSF oscillates with a back-and-forth motion in synchrony with the cardiac and respiratory cycle. The magnitude of these oscillations is variable depending on the specific region of CSF. CSF flow can also be intermittently altered based on various maneuvers such as valsalva, coughing, sneezing, playing a musical instrument, and athletic activities. CSF pressure in a healthy adult is approximately 10 millimeters of mercury in the supine position. CSF pressure is altered in the standing position by hydrostatic pressure gradient along CSF system and can also be transiently affected by maneuvers such as coughing.

Research has indicated that alterations of the biochemical composition of CSF can be indicative and/or involved in the pathological processes of a plethora of central nervous system disease states. For example, in the event of a stroke or other brain trauma, blood can enter the CSF system leading to subsequent injury to the brain due to blood clotting and other biological processes. In context of amyotrophic lateral sclerosis, several chemicals (inflammatory proteins or cytokines such as CHIT1) have been found to be abnormally elevated potentially contributing to the disease pathology. Similarly, in multiple sclerosis proteins, cytokines and chemokines have been found to be elevated and potentially underlying disease progression. As such, in principle, it could be beneficial to remove CSF with abnormal biochemical composition; however, direct removal of CSF is limited as only relatively small amounts can be safely removed. Thus, it can be desirable to remove the CSF from one location (e.g., the cervical region of the spine, or a brain ventricle), alter it (e.g., filter), and return it to the CSF space at a second location (e.g., the lumbar region of the spine). This process can be used to remove the unwanted biochemical products while maintaining similar total CSF volume.

A process termed Neurapheresis may be understood to be the modification of materials (e.g. removal of microorganisms, cells, viruses, foreign material, drugs, combinations thereof, and the like, or circulation and/or addition of materials such as pharmacologic agents) from CSF. This and other therapeutic techniques can be used to treat a number of neurological diseases or conditions, such as Alzheimer's Disease, Parkinson's Disease, Huntington's Disease, Amyotrophic Lateral Sclerosis (ALS), Encephalitis from various causes, Meningitis from various causes, Guillain-Barré Syndrome (GBS), Multiple Sclerosis (MS), HIV-associated neurocognitive disorders, Spinal Cord Injury, Traumatic Brain Injury, cerebral vasospasm, stroke and other diseases or conditions. In addition, a filtering process or system (e.g., a Neurapheresis process or system) can be used during open or endoscopic spine surgery or brain surgery, for example to remove blood that may get in the CSF during the surgery.

FIG. 1 illustrates an example filtering system 10, for example a Neurapheresis filtering system 10. The system 10 may include a controller assembly 12 and a filtering manifold or device 14. In at least some instances, the filtering device 14 includes one or more filters (e.g., such as tangential flow filters, dead-end filters, electrofilters, gravity filters, combinations thereof, and/or the like) generally designed to filter CSF. In at least some instances, the controller assembly 12 may be considered capital equipment for a hospital and/or clinic. In other words, the controller assembly 12 is designed for repeated/multiple uses and/or designed for repeated/multiple interventions and/or designed for repeated/multiple patients. In some of these and in other instances, the filtering device 14 may be considered to be a single-use product. Thus, the filtering device 14 may be designed to be mounted/coupled to controller assembly 12 for a given intervention, used for the intervention, and then removed from the controller assembly 12 when the intervention is completed. The controller assembly 12 can be re-used in a subsequent intervention by mounting/coupling a new filtering device 14 thereto.

Figure 2:
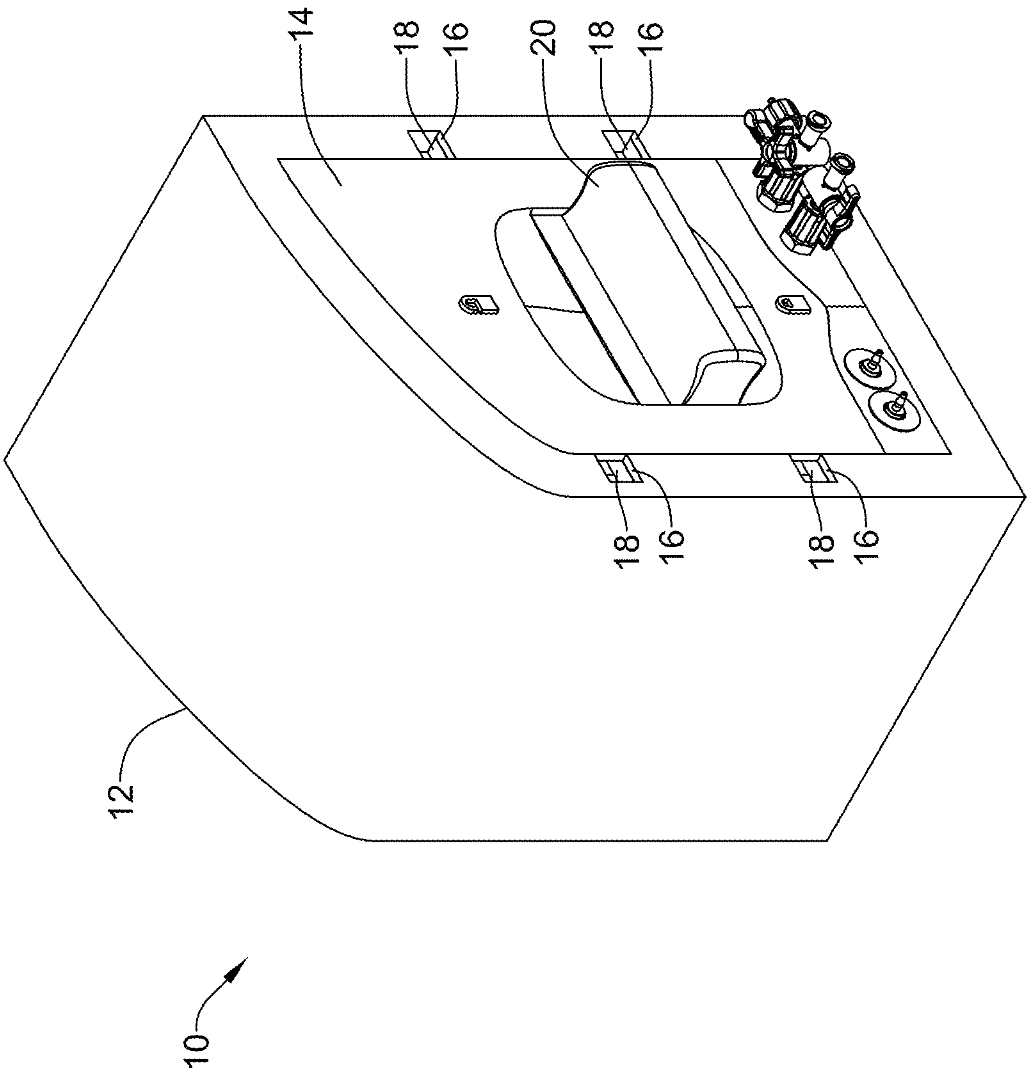
FIG. 2 is a perspective view of a portion of an example filtering system in a second configuration.

In order to efficiently accommodate the mounting/coupling and/or removing of filtering cassette(s) (e.g., like the filtering device 14) thereto, the controller assembly 12 may include a mounting region or socket that is designed to mate with and/or otherwise accommodate the filtering device 14. The socket, along with the corresponding shaped surfaces/housing of the filtering device 14, helps to make mounting/coupling and/or removing the filtering device 14 a relatively straightforward procedure for a clinician. In some instances, the controller assembly 12 may include one or more latching regions 16. The latching regions 16 may be configured to engage or otherwise receive latching projections 18 extending from the filtering device 14. In addition, the filtering device 14 may include a handle 20. The handle 20 may be configured to shift between a first or "unlocked" position (e.g. as depicted in FIG. 1) and a second or "latched" position (e.g., as depicted in FIG. 2). For example, the handle 20 may be coupled to the latching projections 18 so that shifting the handle 20 from the first position to the latched position (e.g., pulling the handle downward) shifts the latching projections 18 into engagement with the latching regions 16 and secures the filtering device 14 to the controller assembly 12. The relatively simple motion of shifting the handle 20 allows a clinician to secure the filtering device 14 to the controller assembly 12 with a single hand.

In use, the system 10 may be used by coupling a catheter (not shown) to the system 10 and disposing the catheter within/along the cerebrospinal space (e.g., such as along lumbar cerebrospinal space). An example catheter may be similar to those disclosed in U.S. Patent Application Pub. No. US 2019/0105475, the entire disclosure of which is herein incorporated by reference. CSF may be removed/aspirated using the catheter and the removed CSF may be processed/filtered using the filtering device 14. The filtered/conditioned CSF may then be returned to the patient using the catheter.

Figure 3:
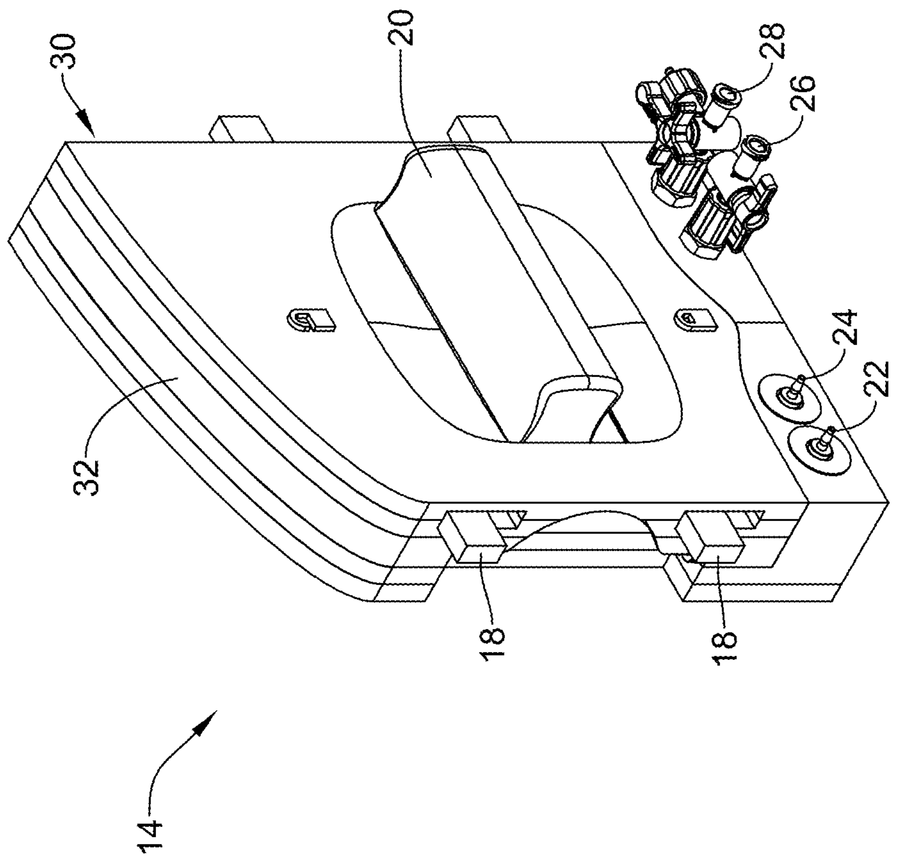
FIG. 3 is a perspective view of an example filtering manifold.

FIG. 3 illustrates the filtering device 14. Here it can be seen that the filtering device 14 may include an inlet 22 (e.g., for receiving cerebrospinal fluid from a patient) and an outlet 24 (e.g., for returning filtered cerebrospinal fluid back to the patient). A catheter or catheter system may be coupled to the inlet 22 and/or the outlet 24. For example, an aspiration lumen of a catheter may be coupled to or in fluid communication with the inlet 22 and an infusion lumen of a catheter (e.g., which may be the same catheter) may be coupled to or in fluid communication with the outlet 24.

The filtering device 14 may also include one or more sampling ports, for example sampling ports 26, 28. The sampling port 26 may be in fluid communication with the inlet 22 such that samples collected at the sampling port 26 may represent CSF collected directly from the patient (e.g., "unfiltered" or "untreated" CSF). Samples collected at the sampling port 26, thus, may be used to analyze the CSF, quantify one or more substances (e.g., pathogens, prokaryotic organisms, eukaryotic organisms, viruses, contaminants, drugs, and/or the like) within the CSF, monitor drug levels in the CSF, monitor progress of a treatment, combinations thereof, and/or the like. The sampling port 28 may be disposed adjacent to the filtering device 14 such that waste material (e.g., material removed/filtered from CSF) can be collected and/or analyzed. Thus, the sampling port 28 may be understood to be in fluid communication with a waste outlet (e.g., a pathway from the filtering device 14 where the waste material is transported). The system 10 may include additional ports that allow for a clinician to assess the filtration during a Neurapheresis procedure. Such sampling ports may be disposed along or in fluid communication with the outlet 24. For example, one or more additional sampling ports may be in fluid communication with the outlet 24 such that samples collected at such a sampling port represent filtered/treated CSF. Thus, collectively, sampling ports are contemplated that can be used to collect (a) unfiltered CSF, (b) filtered/treated CSF, and/or (c) waste material.

The filtering device 14 may also be understood to include a housing 30. The housing 30 may include a curved and/or orienting surface 32. In at least some instances, the curved surface 32 may be disposed along the top of the filtering device 14. The curved surface 32, along with the side surfaces may allow the filtering device 14 to be mounted in a single orientation that avoids misalignment. In other words, the shape of the filtering device 14 (e.g., including the curved surface 32) is configured so that the filtering device 14 can be mounted to the controller assembly 12 in only one orientation.

Figure 4:
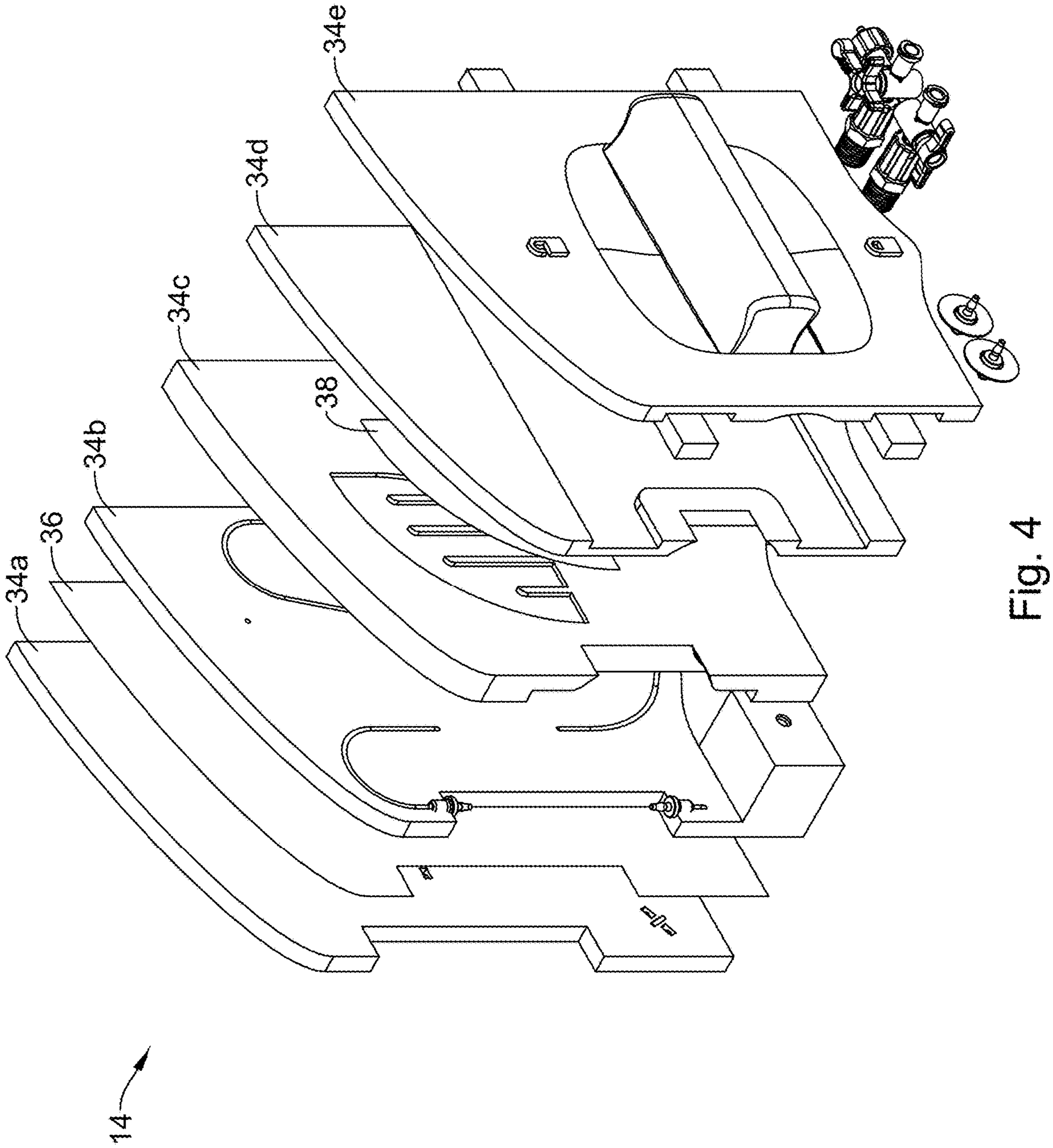
FIG. 4 is an exploded view of an example filtering manifold.

The filtering device 14 and/or housing 30 may include a plurality of layers or plates 34*a*, 34*b*, 34*c*, 34*d*, 34*e* as depicted in exploded view in FIG. 4. In at least some instances, the layers 34*a*, 34*b*, 34*c*, 34*d*, 34*e* may be formed from a suitable polymer/plastic (e.g., acrylic, polycarbonate, etc.). The plurality of layers 34*a*, 34*b*, 34*c*, 34*d*, 34*e* may be coupled, fused, secured, and/or otherwise attached to one another to form/define the housing 30. For simplicity, the layer 34*e* may be referred to the first layer 34*e*, the layer 34*d* may be referred to the second layer 34*d*, the layer 34*c* may be referred to the third layer 34*c*, the layer 34*b* may be referred to the fourth layer 34*b*, and the layer 34*a* may be referred to the fifth layer 34*a*. In at least some instances, a membrane 36 may be disposed between two adjacent layers (e.g., the fifth layer 34*a* and the fourth layer 34*b*). In some of these and in other instances, the membrane 36 could be bonded to the outside of the filter device 14. In general, the membrane 36 may be configured to seal the fluid pathway within the filtering device 14 while allowing pressure to be sensed on/along the outside of the membrane 36. In addition, one or more filter member or disk 38 may be disposed between two adjacent layers (e.g., the third layer 34*c* and the second layer 34*d*).

Figure 5:
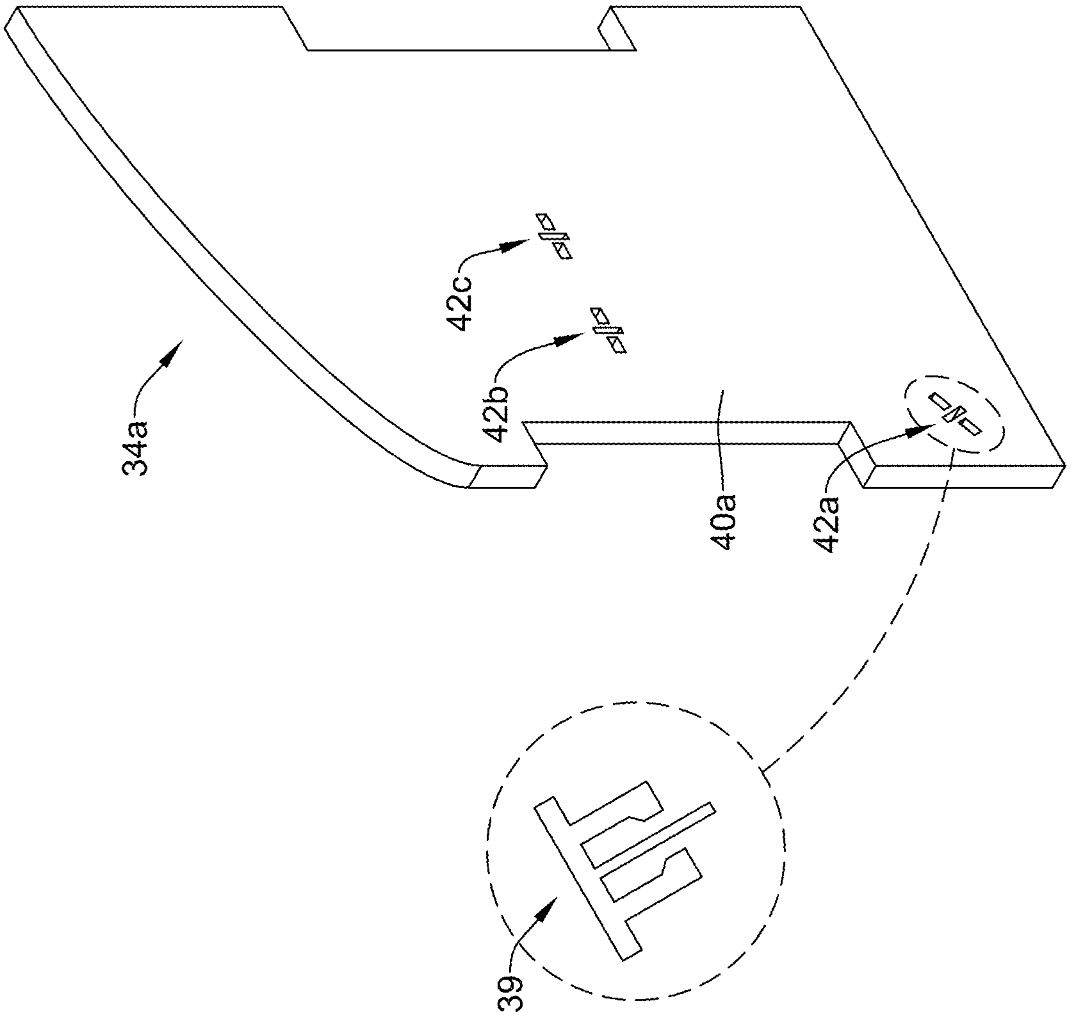
FIG. 5 illustrates a portion of an example filtering manifold.
Figure 6:
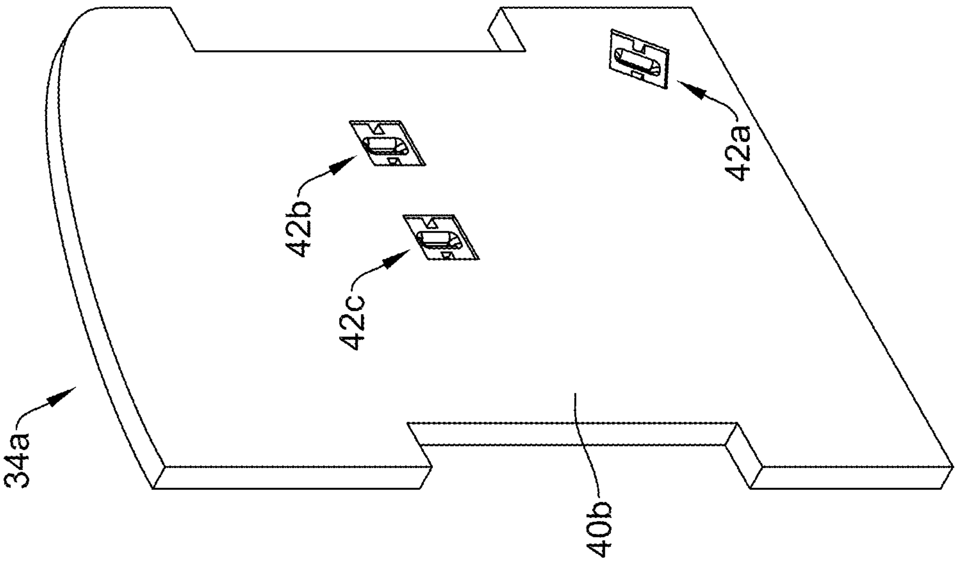
FIG. 6 illustrates a portion of an example filtering manifold.
Figure 7:
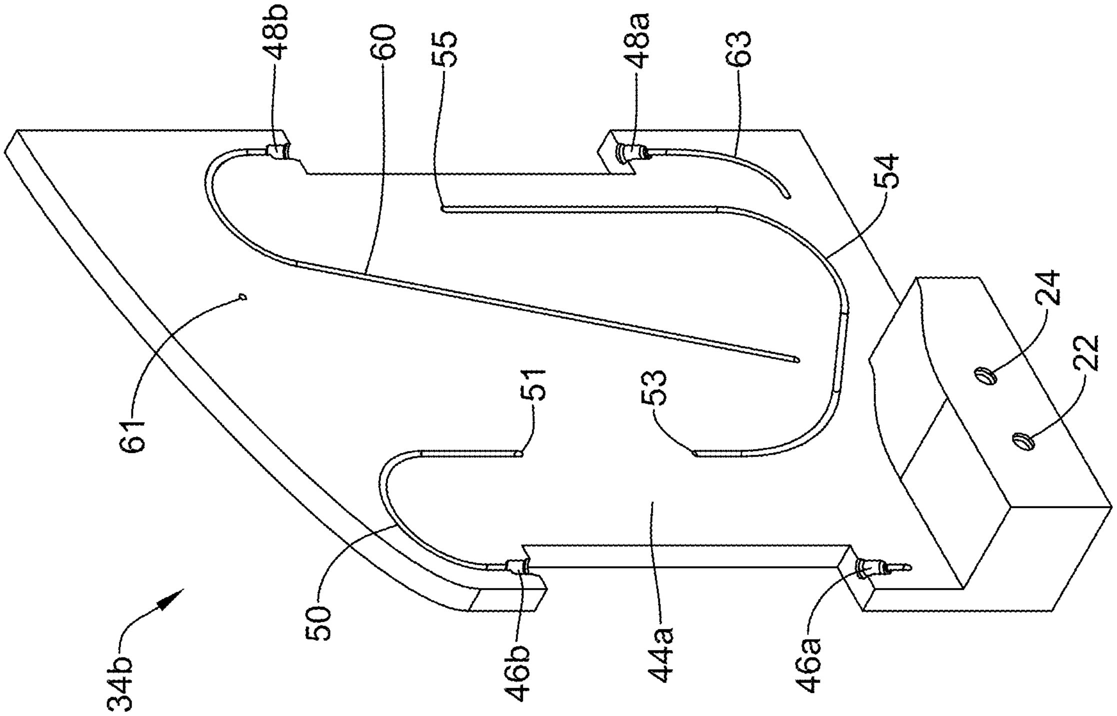
FIG. 7 illustrates a portion of an example filtering manifold.
Figure 9:
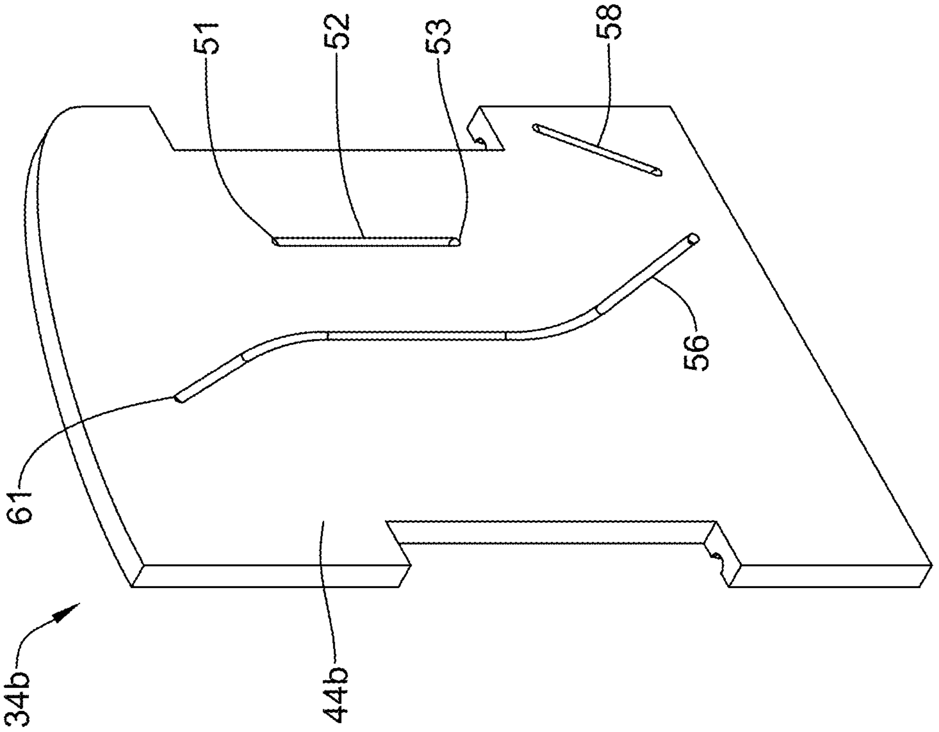
FIG. 9 illustrates a portion of an example filtering manifold.
Figure 10:
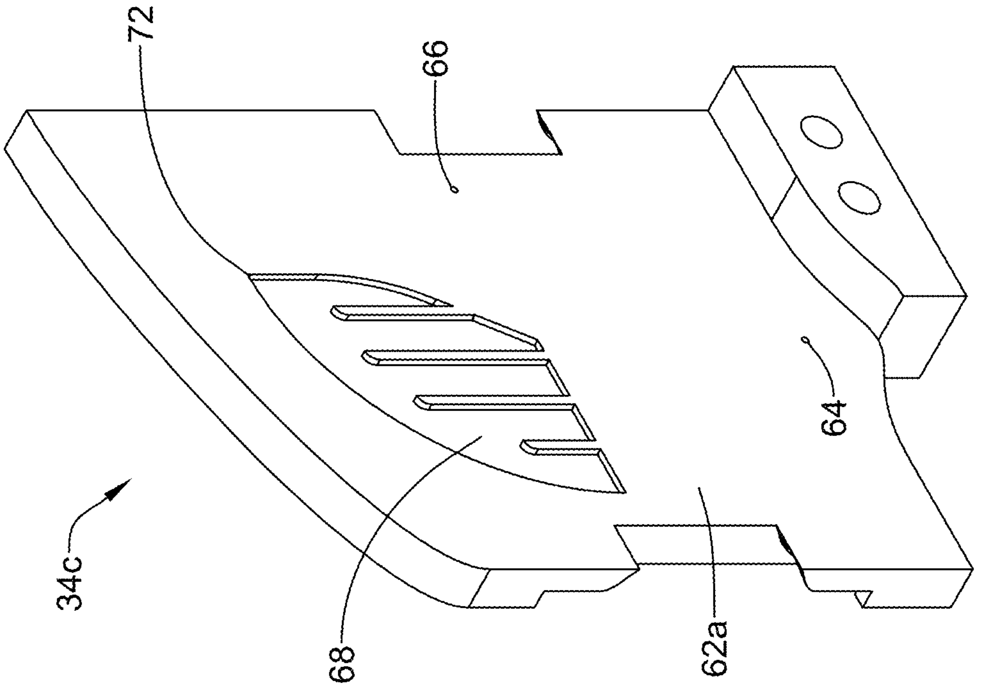
FIG. 10 illustrates a portion of an example filtering manifold.
Figure 11:
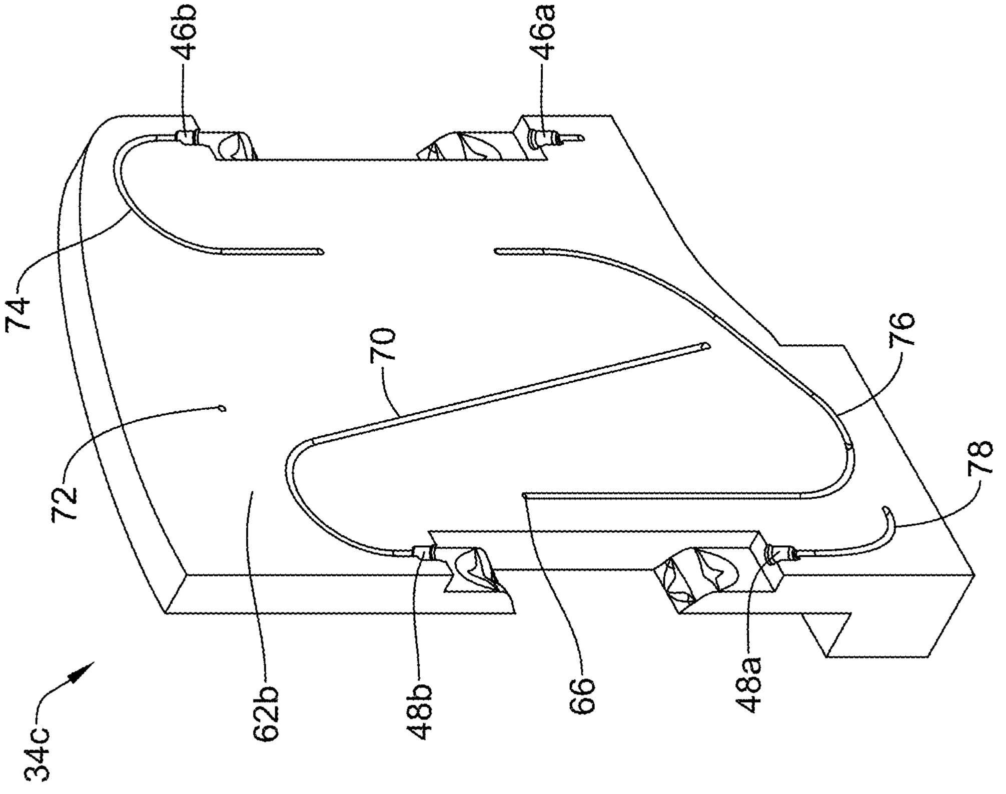
FIG. 11 illustrates a portion of an example filtering manifold.
Figure 12:
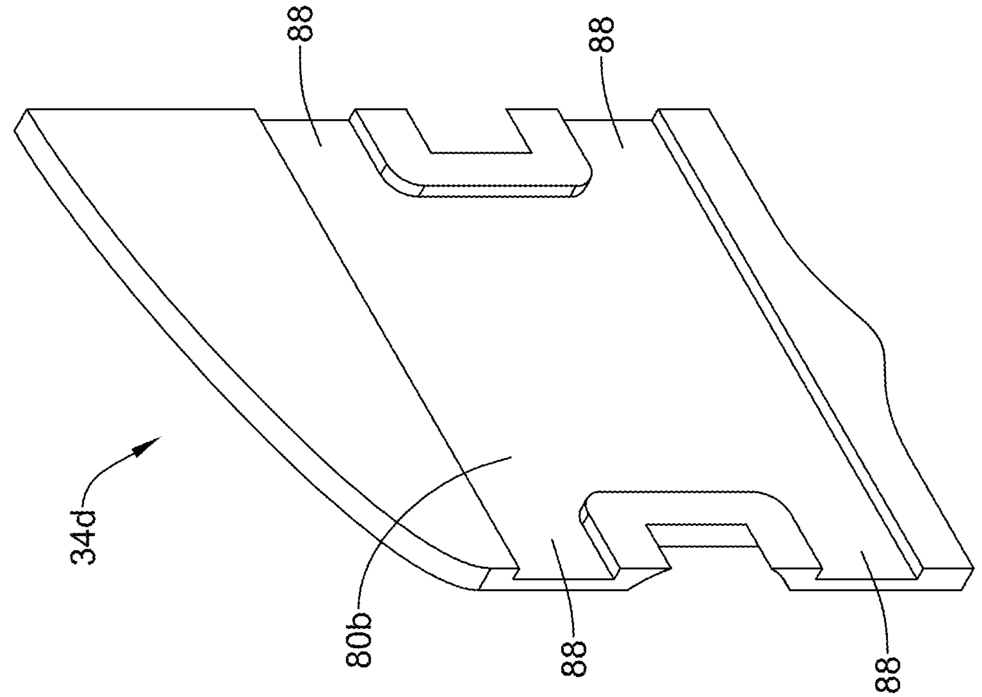
FIG. 12 illustrates a portion of an example filtering manifold.
Figure 13:
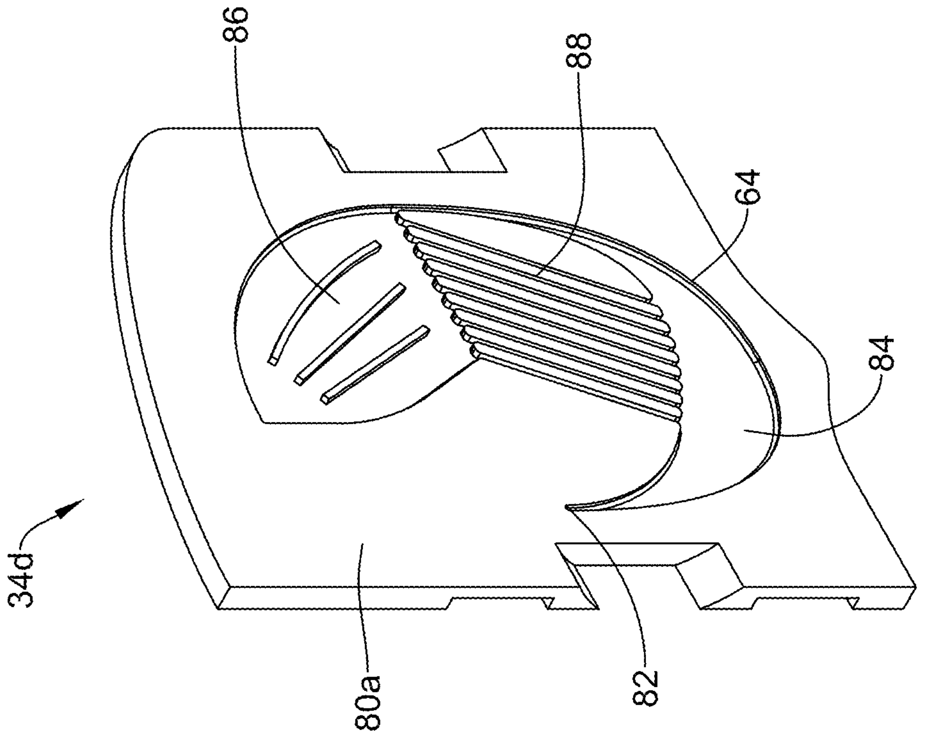
FIG. 13 illustrates a portion of an example filtering manifold.
Figure 14:
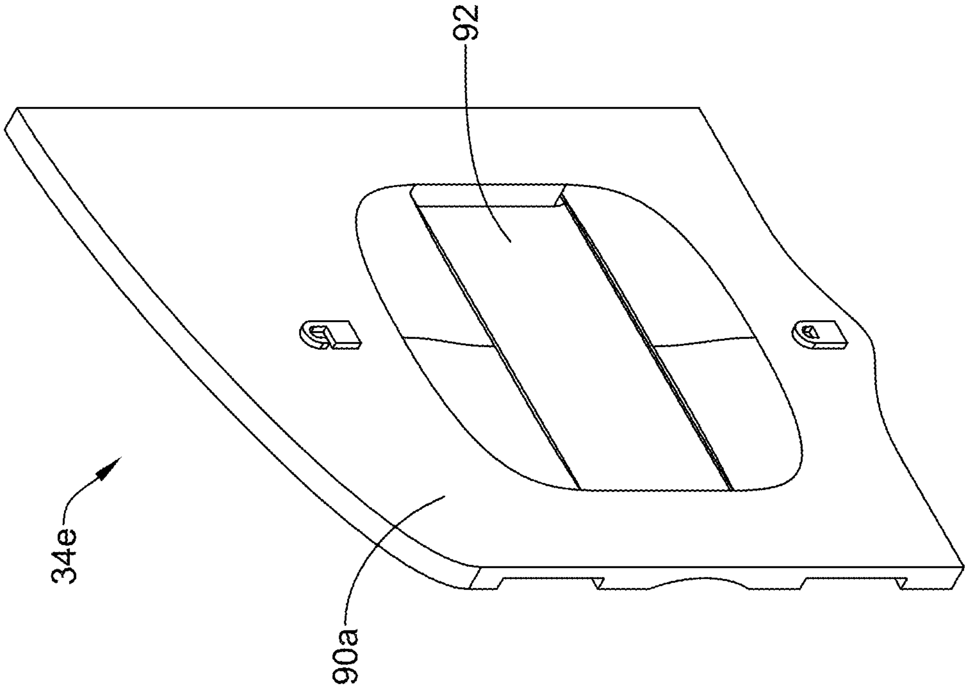
FIG. 14 illustrates a portion of an example filtering manifold.
Figure 15:
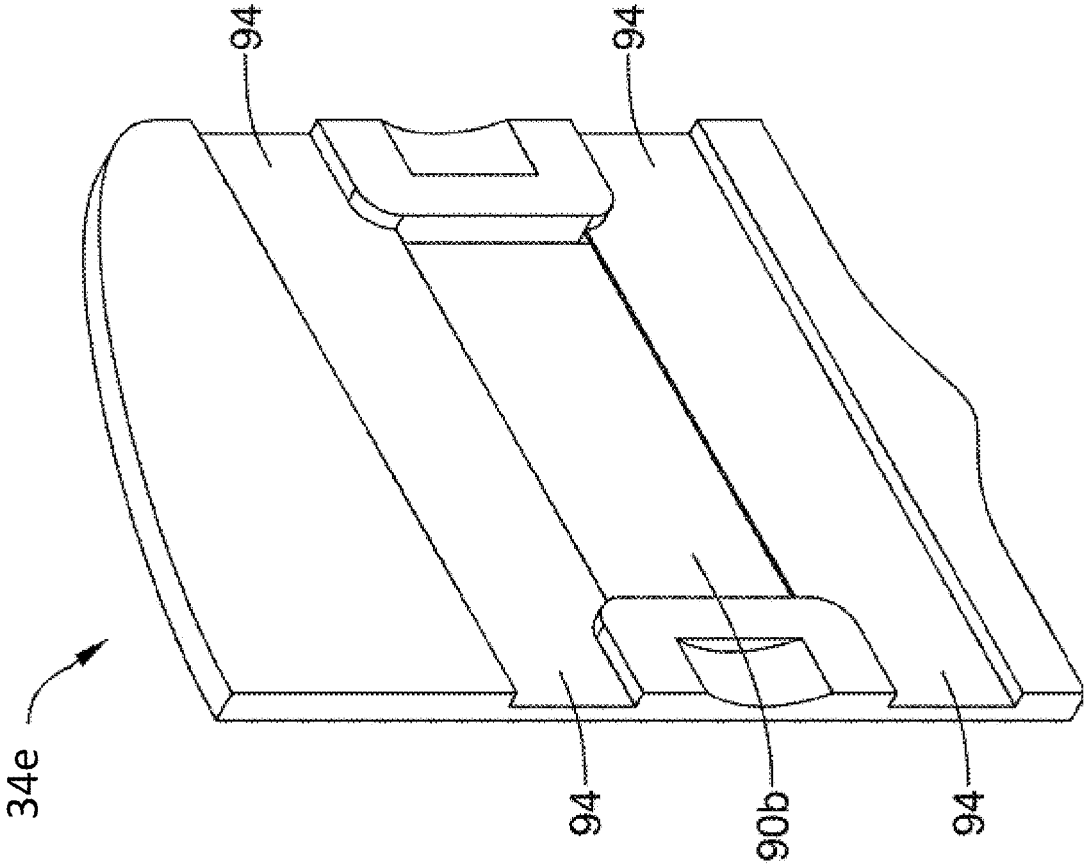
FIG. 15 illustrates a portion of an example filtering manifold.

FIGS. 5-6 illustrate front and rear view of the fifth layer 34*a*. FIGS. 7 and 9 illustrate front and rear view of the fourth layer 34*b*. FIGS. 10-11 illustrate front and rear view of the third layer 34*c*. FIGS. 12-13 illustrate front and rear view of the second layer 34*d*. FIGS. 14-15 illustrate front and rear view of the first layer 34*e*. When assembled, a number of grooves, cutouts, slots, and/or openings formed in the layers 34*a*, 34*b*, 34*c*, 34*d*, 34*e* generally define a fluid pathway therethrough between the inlet 22 and the outlet 24. The grooves, cutouts, slots, and/or openings formed in the layers 34*a*, 34*b*, 34*c*, 34*d*, 34*e* by a suitable process such as injection molding, machining, etching, and/or the like. Joining of the layers 34*a*, 34*b*, 34*c*, 34*d*, 34*e* (which may include thermal bonding, welding, ultrasonic welding, heat fusion welding, adhesive bonding, mechanically bonding, and/or the like) may form a fluid-tight seal that helps to contain the fluid pathway within the filtering device 14. The various layers 34*a*, 34*b*, 34*c*, 34*d*, 34*e* will be discussed collectively along with fluid pathway.

Beginning with the fifth layer 34*a*, here it can be seen that the fifth layer 34*a* may include a front surface 40*a* and a rear surface 40*b*. A plurality of openings and/or sensor regions 42*a*, 42*b*, 42*c* (which each may house a float 39 that may contact the membrane 36 to transfer pressure from the fluid pathway to a pressure sensor that may be disposed on or coupled to the controller assembly 12) may be disposed along the fifth layer 34*a* (see, for example, FIGS. 5-6).

Figure 8:
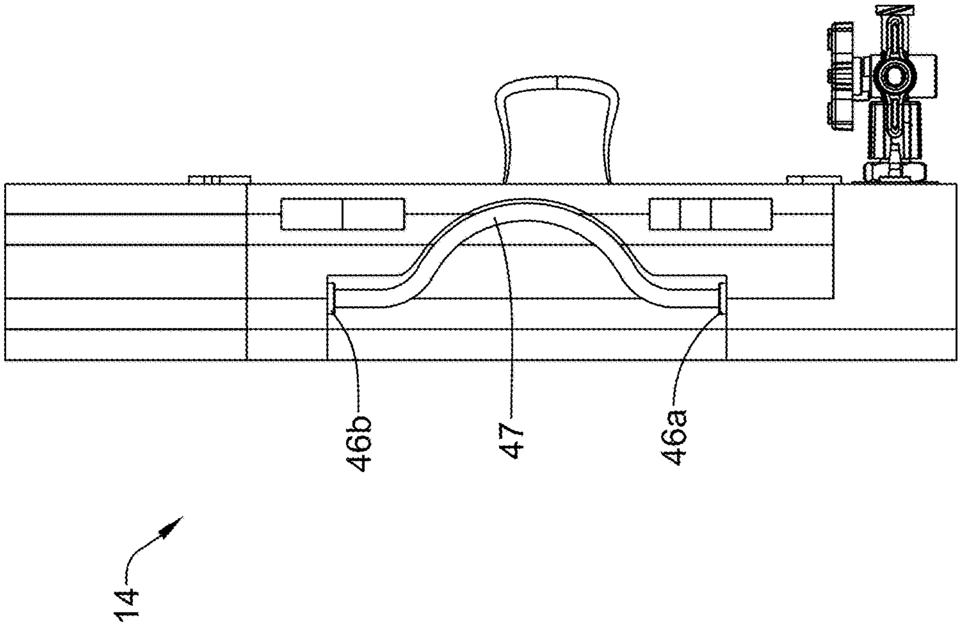
FIG. 8 is a side view of an example filtering manifold.

Similarly, the fourth layer 34*b* may include a front surface 44*a* and a rear surface 44*b* (see, for example, FIGS. 7-8). The fourth layer 34*b* may include a first port region 46*a* in fluid communication with the inlet 22. The first port region 46*a* may also be seen along the rear of the third layer 34*c* (see, for example, FIG. 11). Between the first port region 46*a* and the inlet, fluid may travel along a region 58 (see, for example, FIG. 9) and across the sensor region 42*a* (which each may house a float 39 that may contact the membrane 36 to transfer pressure from the fluid pathway to a pressure sensor that may be disposed on or coupled to the controller assembly 12) so that inlet/inflow pressure can be measured/monitored. The fluid may travel from the first port region 46*a* along the exterior of the filtering device 14 to a second port region 46*b* through a tube 47 as shown in FIG. 8. The port regions 46*a,* 46*b* may also be termed connectors or connector regions where the tube 47 may be connected. The tube 47 may follow an arcuate surface of the filtering device 14 (e.g., and/or the housing 30) and the tube 47 may be configured to be engaged by a pumping mechanism (e.g., peristaltic pumping mechanism) or roller (e.g., which may be a component of the controller assembly 12) to facilitate movement of fluid along the fluid pathway. In at least some instances, the portion of the filtering device 14 adjacent to the port regions 46*a,* 46*b* and the tube 47 may be termed a pump region.

After passing through the second port region 46*b,* the fluid may continue along region 50 (and corresponding region 74 along the rear surface 62*b* of the third layer 34*c;* thus the fluid pathway may be described as being between the fourth layer 34*b* and the third layer 34*c*) and through an opening 51 to the rear side of the fourth layer 34*b* to travel along region 52. Here, the fluid may travel across the sensor region 42*b* (which may house a float 39 that may contact the membrane 36 to transfer pressure from the fluid pathway to a pressure sensor that may be disposed on or coupled to the controller assembly 12) so that pressure (e.g., filter pressure) can be measured/monitored. The fluid may pass through another opening 53 back to the front side if the fourth layer 34*b* to travel along region 54 (and corresponding region 76 along the rear of the third layer 34*c*). In some instances, the fluid may be sampled along region 54 (e.g., along the bottom of the arc of region 54) at a sampling port.

The fluid traveling along region 54 of the fourth layer 34*b* and along region 76 of the third layer 34*c* to a position 55, and through an opening 66 in the third layer 34*c*. Here, the fluid pathway may generally be understood as being between the third layer 34*c* and the second layer 34*d* (e.g., the second layer 34*d* may include a front surface 80*a* and a rear surface 80*b*) and the fluid may undergo a number of filtering steps/processes. For example, the fluid may enter region 82 and travel along a widened region 84. The widened region 84 may be configured to slow the passage of fluid therethrough. In some instances, the widened region 84 may be configured to slow the passage of fluid by 10-1000%, or by about 50-800%, or by about 100-600%, or by about 200-500%, or by about 400%. by slowing the passage of fluid, materials carried by the fluid such as blood or blood cells may being to settle or drop toward the bottom of the widened region 84. Because of this, the widened region 84 may include or otherwise define a gravity filtration region. In some instances, a waste outlet 64 may be defined at the bottom of the widened/gravity filtration region 84 (e.g., see FIG. 10). The fluid may travel along region 88 to a filtering region 86 (and corresponding filtering region 68 along the front surface 62*a* of the third layer 34*c*). Here, the fluid may pass through the filter member 38 (which may be trapped or otherwise positioned between the second layer 34 and the third layer 34*c*). In at least some instances, the filter member 38 is a dead-end filter. Other types of filters are contemplated. Filtered fluid may pass through an opening 72 in the third layer 34*c,* through an opening 61 in the fourth layer 34*b,* along region 56, and to the outlet 24. When doing so, the fluid may travel across the sensor region 42*c* (which each may house a float 39 that may contact the membrane 36 to transfer pressure from the fluid pathway to a pressure sensor that may be disposed on or coupled to the controller assembly 12) so that pressure (e.g., return pressure) can be measured/monitored.

Waste may travel from waste outlet 64 to/along region 60 (and corresponding region 70 along the third layer 34*c*). The waste may travel through a first port region 48*b* through a tube (not shown, but may be similar to the tube 47) along the exterior of the filtering device 14, to a second portion region 48*a,* to a waste region 63 (and corresponding region 78 along the rear of third layer 34*c*) to a sampling port/waste outlet.

Finally, FIGS. 14-15 illustrate the first layer 34*e,* showing the front surface 90*a* and the rear surface 90*b*. Also shown in an opening 92 for the handle 20 to extend through. The first layer 34*e* may also include grooves or channels 94 (along with corresponding grooves or channels 88 along the second layer 34*d*) for accommodating the latching projections 18.

U.S. Patent Application No. 63/022,733 is herein incorporated by reference.

U.S. Patent Application Pub. No. US 2019/0105475 is herein incorporated by reference.

U.S. patent application Ser. No. 15/367,592 is herein incorporated by reference.

U.S. Pat. No. 10,632,237 is herein incorporated by reference.

U.S. patent application Ser. No. 15/177,638 is herein incorporated by reference.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A filtering cassette for use with a cerebrospinal fluid system, the filtering cassette comprising:

a filter housing formed from a plurality of discrete layers coupled together and defining a fluid pathway therein;

wherein the plurality of discrete layers includes a first layer having a first groove formed therein and an adjacent second layer having a second groove formed therein wherein the first groove and the second groove are aligned to define a portion of the fluid pathway:

a membrane disposed between two adjacent layers of the filter housing;

a filtering section defined by a widened region of the fluid pathway that is configured to slow the passage of fluid therethrough in order to allow gravity filtration of fluid passing therethrough, wherein the widened region is formed between a recess in the first layer and a flat surface of the adjacent second layer; and a waste outlet defined through the adjacent second layer at the bottom of the widened region.

2. The filtering cassette of claim 1, further comprising a filter disk member disposed between the two adjacent layers of the filter housing.

3. The filtering cassette of claim 2, wherein the filter disk member includes a dead-end filter disk.

4. The filtering cassette of claim 1, further comprising one or more sensors coupled to the filter housing.

5. The filtering cassette of claim 1, further comprising a sampling port.

6. The filtering cassette of claim 1, wherein the filter housing includes three or more layers.

7. The filtering cassette of claim 1, wherein the filter housing includes four or more layers.

8. The filtering cassette of claim 1, wherein the filter housing includes five or more layers.

9. The filtering cassette of claim 1, further comprising a handle coupled to the filter housing.

10. The filtering cassette of claim 9, wherein the handle includes one or more latching projections, wherein the handle is configured to shift between a first position and a second position.

11. A filtering cassette for use with a cerebrospinal fluid system, the filtering cassette comprising:

a plurality of plates coupled together to define a filter housing having a fluid pathway formed therein;

wherein the plurality of plates includes a first plate having a first groove formed therein and an adjacent second plate having a second groove formed therein;

wherein the first groove and the second groove are aligned to define a portion of the fluid pathway:

a membrane disposed between two adjacent plates of the plurality of plates;

a filtering section defined by a widened region of the fluid pathway that is configured to slow the passage of fluid therethrough in order to allow gravity filtration of fluid passing therethrough, wherein the widened region is formed between a recess in the first plate and a flat surface of the adjacent second plate; and a waste outlet defined through the adjacent second plate at the bottom of the widened region.

12. The filtering cassette of claim 11, further comprising a float coupled to one of the plates that contacts the membrane.

13. The filtering cassette of claim 11, further comprising a filter disk member disposed between two adjacent layers of the filter housing.

14. The filtering cassette of claim 13, wherein the filter disk member includes a dead-end filter disk.

15. The filtering cassette of claim 11, further comprising one or more sensors coupled to the filter housing.

16. The filtering cassette of claim 11, further comprising a sampling port.

17. The filtering cassette of claim 11, further comprising a handle coupled to the filter housing.

18. The filtering cassette of claim 17, wherein the handle includes one or more latching projections, wherein the handle is configured to shift between a first position and a second position.

19. A cerebrospinal fluid filtering system, the system comprising:

a controller assembly;

a filtering cassette removably coupled to the controller assembly; and wherein the filtering cassette comprises: a filter housing formed from a plurality of plates coupled together and defining a fluid pathway therein, a membrane disposed between two adjacent layers of the filter housing, wherein the plurality of plates includes a first plate having a first groove formed along a front surface thereof and an adjacent second plate having a second groove formed along a rear surface thereof;

wherein the first groove and the second groove are aligned to define a portion of the fluid pathway;

a filtering section defined by a widened region of the fluid pathway that is configured to slow the passage of fluid therethrough in order to allow gravity filtration of fluid passing therethrough, wherein the widened region is formed between a recess in the first plate and a flat surface of the adjacent second plate; and a waste outlet defined through the adjacent second plate at the bottom of the widened region.

20. The cerebrospinal fluid filtering system of claim 19, wherein the widened region is configured to slow the passage of the fluid therethrough by 100-1000%.

* * * * *